(12) United States Patent
Ohdachi

(10) Patent No.: US 6,375,619 B1
(45) Date of Patent: Apr. 23, 2002

(54) ULTRASONIC DIAGNOSTIC APPARATUS

(75) Inventor: Ichiro Ohdachi, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/698,439

(22) Filed: Oct. 27, 2000

(30) Foreign Application Priority Data

Oct. 28, 1999 (JP) .............................. 11-307346
Jul. 24, 2000 (JP) ...................... 2000-222768

(51) Int. Cl.⁷ ................................................ A61B 8/00
(52) U.S. Cl. ........................................ 600/459; 600/460
(58) Field of Search ..................... 600/443, 459, 600/460, 462, 107, 437, 440; 606/329

(56) References Cited

U.S. PATENT DOCUMENTS 5,542,425 A    8/1996  Marshall et al.
5,855,556 A *  1/1999  Shirai ........................ 600/440
6,261,297 B1 * 7/2001  Kadziauskas et al. ....... 600/107

* cited by examiner

Primary Examiner—Francis J. Jaworski
Assistant Examiner—Maulin Patel
(74) Attorney, Agent, or Firm—Scully, Scott, Murphy & Presser

(57) ABSTRACT

A PC base ultrasonic diagnostic apparatus comprises an apparatus main body and an ultrasonic scope detachably attached to the main body. The apparatus main body includes a power switch for turning on and off a power supply for the entire apparatus, a connector section connected to the scope-side connector of the ultrasonic scope, and a scope connector switch for allowing and interrupting the supply of power from a power supply section to the connector section.

14 Claims, 13 Drawing Sheets

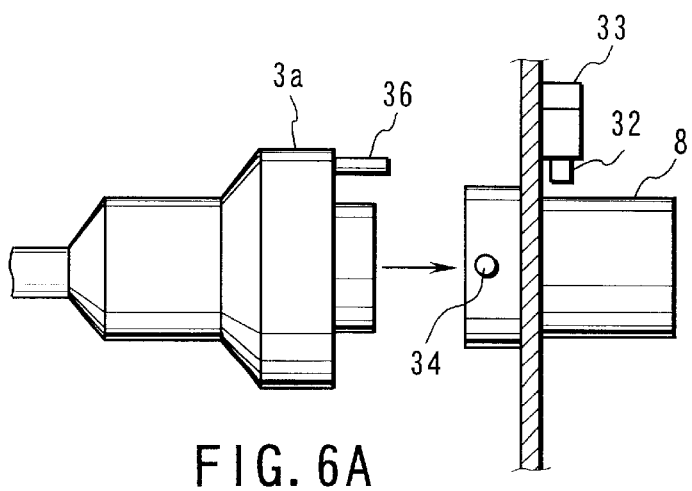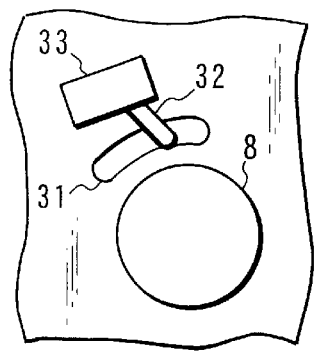
FIG. 6A    FIG. 6B
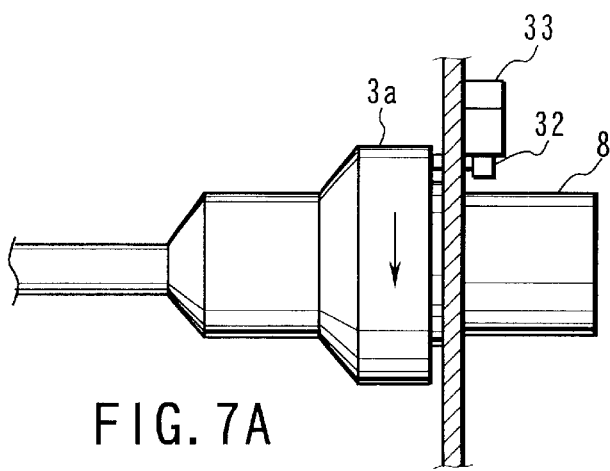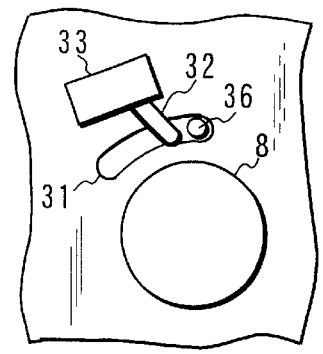
FIG. 7A    FIG. 7B
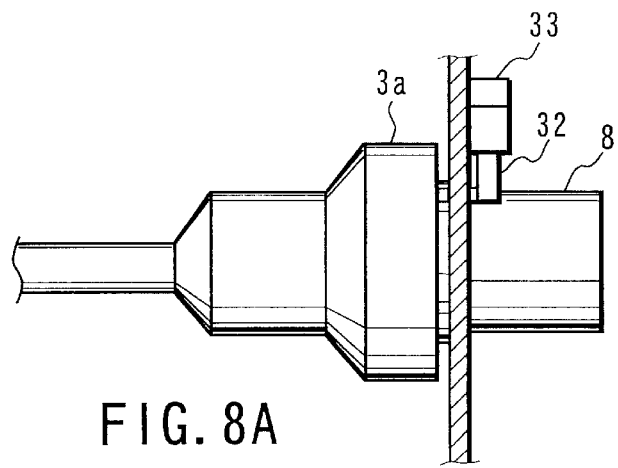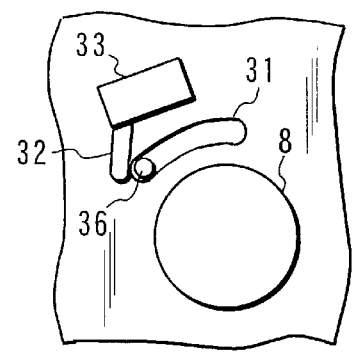
FIG. 8A    FIG. 8B

ULTRASONIC DIAGNOSTIC APPARATUS

CROSS-REFERENCE TO RELATED APPLICATIONS

This application is based upon and claims the benefit of priority from the prior Japanese Patent Applications No. 11-307346, filed Oct. 28, 1999; and No. 2000-222768, filed Jul. 24, 2000, the entire contents of which are incorporated herein by reference.

BACKGROUND OF THE INVENTION

This invention relates to an ultrasonic diagnostic apparatus, and more particularly to an ultrasonic diagnostic apparatus characterized by a control section for controlling a power supply for an ultrasonic scope.

To facilitate downsizing, adding functions at low cost, etc., a so-called PC base (Personal Computer base) ultrasonic diagnostic apparatus is now being developed, in which the functions of a conventional coordinate conversion circuit, interpolation circuit, controller, etc. are executed using a computer board.

In the prior art, when attaching or detaching an ultrasonic scope or an ultrasonic probe to or from a diagnostic apparatus, it should be noted that the apparatus is turned off in order to prevent breakage of a circuit in the apparatus.

However, the PC base ultrasonic diagnostic apparatus generally requires a lot of time until it shifts to a diagnosis enabled state after it is turned on. If the apparatus is turned off to exchange a scope or a probe for a new one while it executes a diagnosis, the diagnosis is interrupted for a long time.

BRIEF SUMMARY OF THE INVENTION

It is the object of the invention to provide an ultrasonic diagnostic apparatus, which prevents an apparatus main body and an ultrasonic scope incorporated therein from breakage of a circuit when attaching or detaching the ultrasonic scope to or from the apparatus main body, and which reduces the time required for exchanging scopes, i.e. the downtime of a diagnosis.

The invention claimed in claim 1 provides an ultrasonic diagnostic apparatus comprising: a casing; a power supply section; an ultrasonic scope having a connector at an end thereof and adapted to transmit and receive an ultrasonic wave; a connector section provided at the casing to which the connector of the ultrasonic scope is detachably attached; an auxiliary switch for allowing and interrupting supply of power from the power supply section to the connector section; and ultrasonic signal processing means for supplying the ultrasonic scope with an ultrasonic wave and processing an echo signal of the ultrasonic wave when power is supplied to the connector section.

The above structure prevents the apparatus main body and the ultrasonic scope from breakage of a circuit when attaching or detaching the ultrasonic scope to or from the apparatus main body, and reduces the time required for exchanging scopes, i.e. the downtime of a diagnosis.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 6A and 6B are views useful in explaining the operation of the PC base ultrasonic diagnostic apparatus of FIG. 5;

FIGS. 7A and 7B are views useful in explaining the operation of the PC base ultrasonic diagnostic apparatus of FIG. 5;

FIGS. 8A and 8B are views useful in explaining the operation of the PC base ultrasonic diagnostic apparatus of FIG. 5;

DETAILED DESCRIPTION OF THE INVENTION

The embodiments of the invention will be described with reference to the accompanying drawings.
(First Embodiment)

Figure 1:
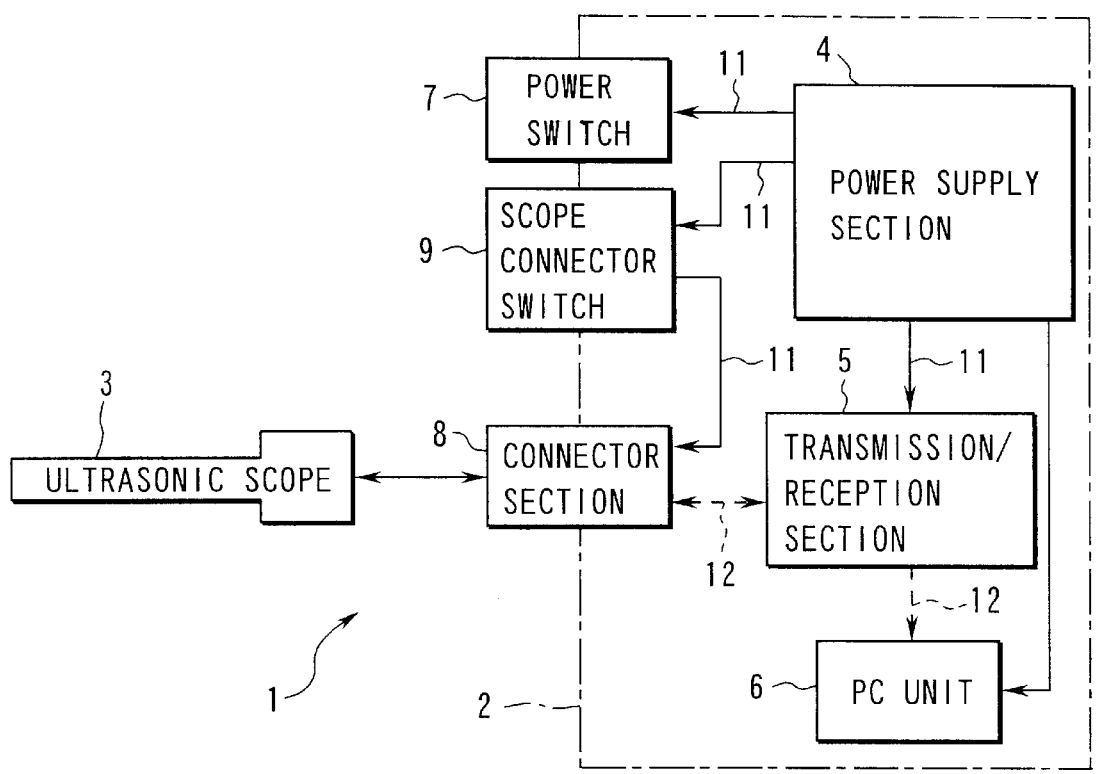
FIG. 1 is a block diagram illustrating a PC base ultrasonic diagnostic apparatus according to a first embodiment of the invention.
Figure 2:
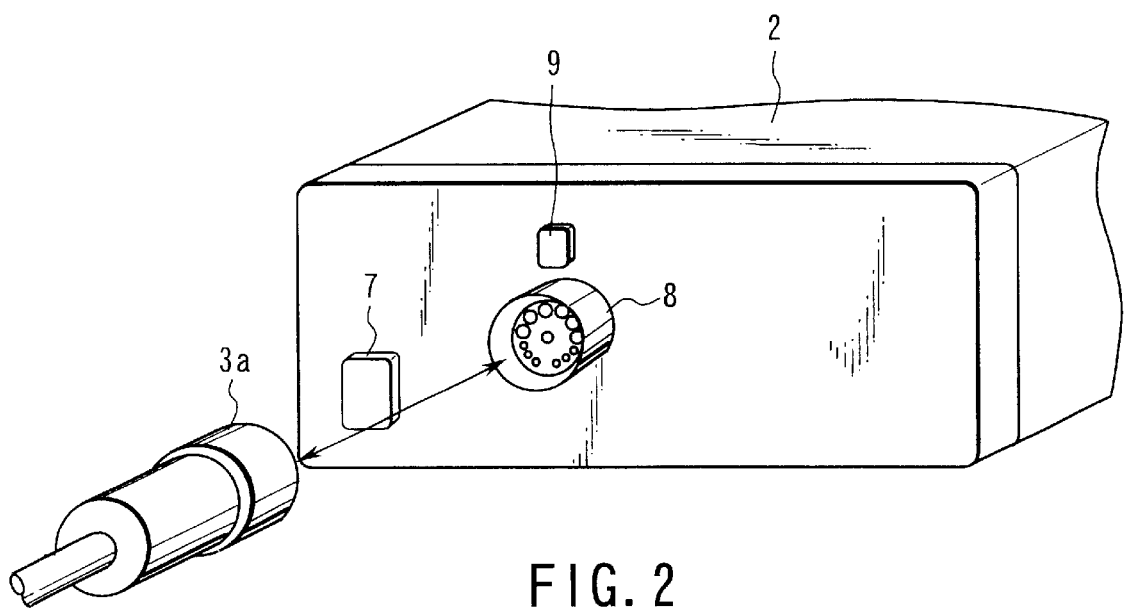
FIG. 2 is a perspective view illustrating an external appearance of the PC base ultrasonic diagnostic apparatus of FIG. 1.

FIGS. 1 and 2 relate to a first embodiment of the invention. FIG. 1 is a block diagram showing a PC base ultrasonic diagnostic apparatus according to the first embodiment, while FIG. 2 is a perspective view illustrating an external appearance of the PC base ultrasonic diagnostic apparatus of FIG. 1.

AS is shown in FIG. 1, a PC base ultrasonic diagnostic apparatus 1 according to the first embodiment comprises an apparatus main body 2, and an ultrasonic scope 3 detachably attached to the main body 2. The apparatus main body 2 includes a power supply section 4 for supplying power to every section incorporated therein; a transmission/reception section 5 as ultrasonic signal processing means for transmitting a transmission pulse signal to the oscillator of the ultrasonic scope 3, and receiving a reflection signal generated from the oscillator; and a PC unit 6 for executing processing for constructing an ultrasonic tomogram based on the reflection signal received by the transmission/reception section 5, and controlling the entire apparatus.

The apparatus main body 2 further comprises a power switch 7 for starting and stopping the supply of power to the entire apparatus; a connector section 8 to be connected to a scope-side connector 3a (see FIG. 2) incorporated in the ultrasonic scope 3; and a scope connector switch 9 as an auxiliary switch for starting and stopping the supply of power from the power supply section 4 to the connector section 8.

In the apparatus main body 2, the power supply section 4 and the connector section 8 are connected each other, via the scope connector switch 9, by means of a power supply line 11 (indicated by a solid line in FIG. 1) for supplying power from the power supply section 4. Further, the connector section 8 and the transmission/reception section 5 are connected to each other by a signal line 12 (indicated by the broken line) for transmitting a transmission pulse signal to the oscillator of the ultrasonic scope 3, and receiving a reflection signal generated from the oscillator. As shown in FIG. 2, the scope connector switch 9 is provided near the connector section 8.

The operation of the apparatus will be described. When executing an ultrasonic diagnosis using the PC base ultrasonic diagnostic apparatus of the first embodiment, at first, the apparatus main body 2 is excited by turning on the power switch 7, thereby attaching the scope-side connector 3a of the ultrasonic scope 3 to the connector section 8 of the main body 2. At this time, the terminal of the connector section 8 is brought into contact with the terminal of the scope-side connector 3a, whereby the ultrasonic scope 3 is electrically connected to the apparatus main body 2.

After that, the scope connector switch 9 is pushed to start the supply of power from the power supply section 4 to the connector section 8. In this state, power is supplied from the power supply section 4 to the connector section 8 via the power supply line 11, thereby enabling the use of the ultrasonic scope 3.

A transmission pulse signal is supplied from the transmission/reception section 5 to the connector section 8 via the signal line 12, and then to the oscillator of the ultrasonic scope 3. A reflection signal is supplied from the oscillator to the connector section 8 via the signal line, and then to the PC unit 6, where it is processed to display an ultrasonic image on a monitor (not shown).

When exchanging, during a diagnosis, the ultrasonic scope 3 for another one having, for example, a different frequency, the supply of power to the connector section 8 is stopped by pushing the scope connector switch 9, thereby detaching the ultrasonic scope 3 from the connector section 8. At this time, the terminal of the connector section 8 is separated from that of the scope-side connector 3a, thereby electrically disconnecting the ultrasonic scope 3 from the apparatus main body 2. At this time, the supply of power to the connector section 8 is interrupted, whereas any other section is supplied with power. In this state, another scope is connected to the connector section 8, and the scope connector switch 9 is pushed to turn on the connector section 8.

When exchanging the ultrasonic scope 3 for another in the first embodiment, the scope 3 and the main body 2 are prevented from breakage by interrupting the supply of power to the connector section 8. Since, at this time, the scopes can be exchanged with the supply of power to any section other than the connector section 8 maintained, the downtime of a diagnosis can be minimized.
(Second Embodiment)

Figure 3:
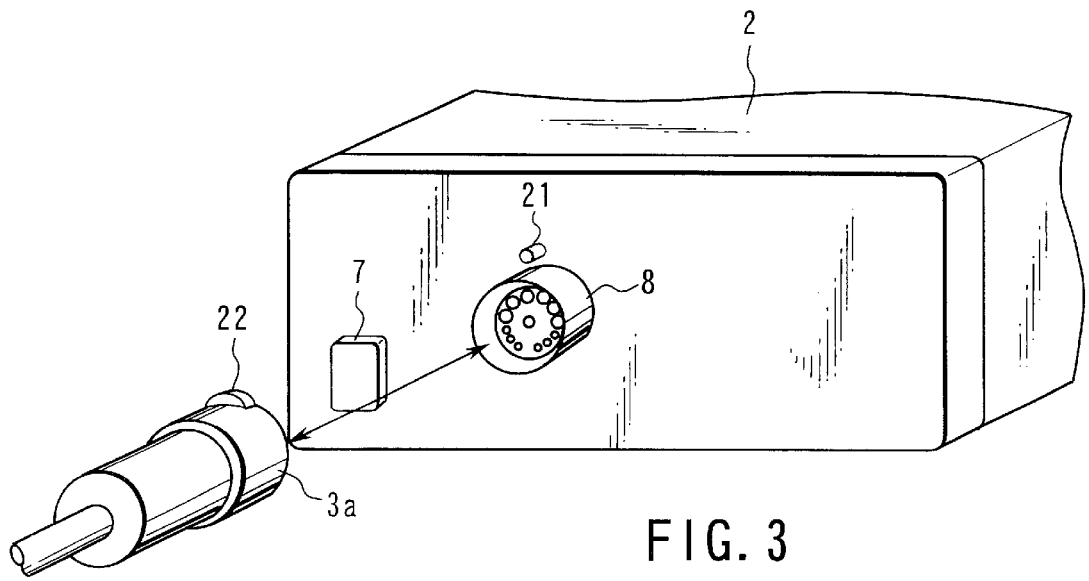
FIG. 3 is a perspective view illustrating an external appearance of a PC base ultrasonic diagnostic apparatus according to a second embodiment of the invention.
Figure 4A:
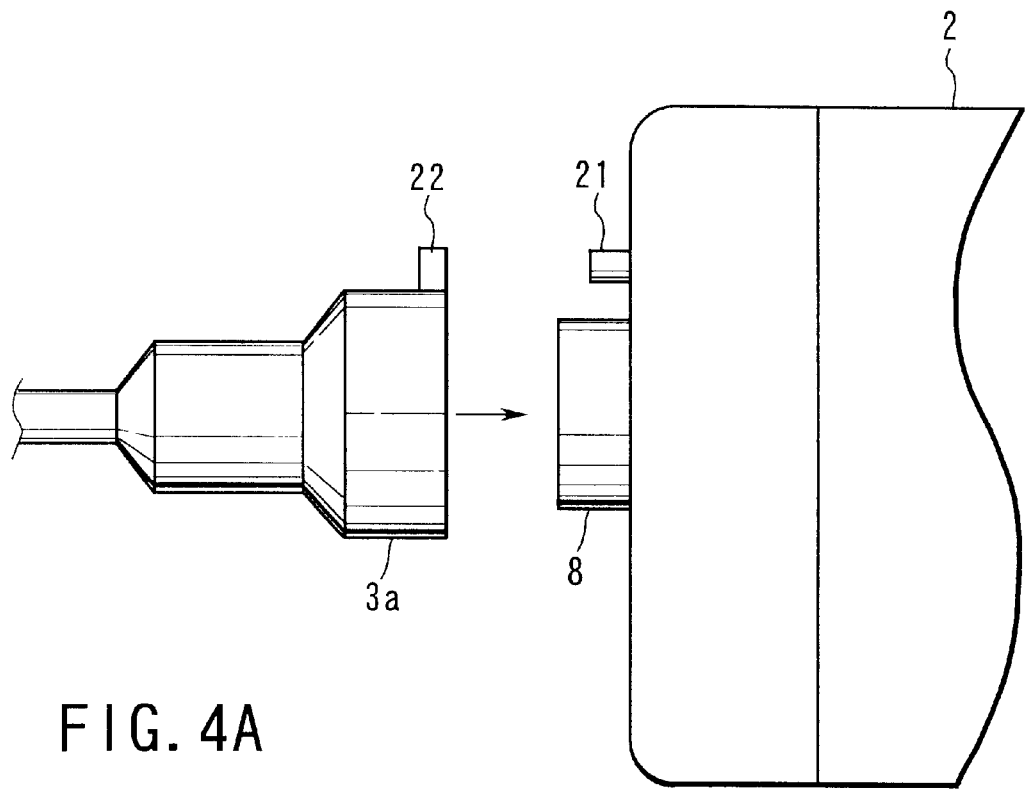
FIGS. 4A and 4B are views useful in explaining the operation of the PC base ultrasonic diagnostic apparatus of FIG. 3.
Figure 4B:
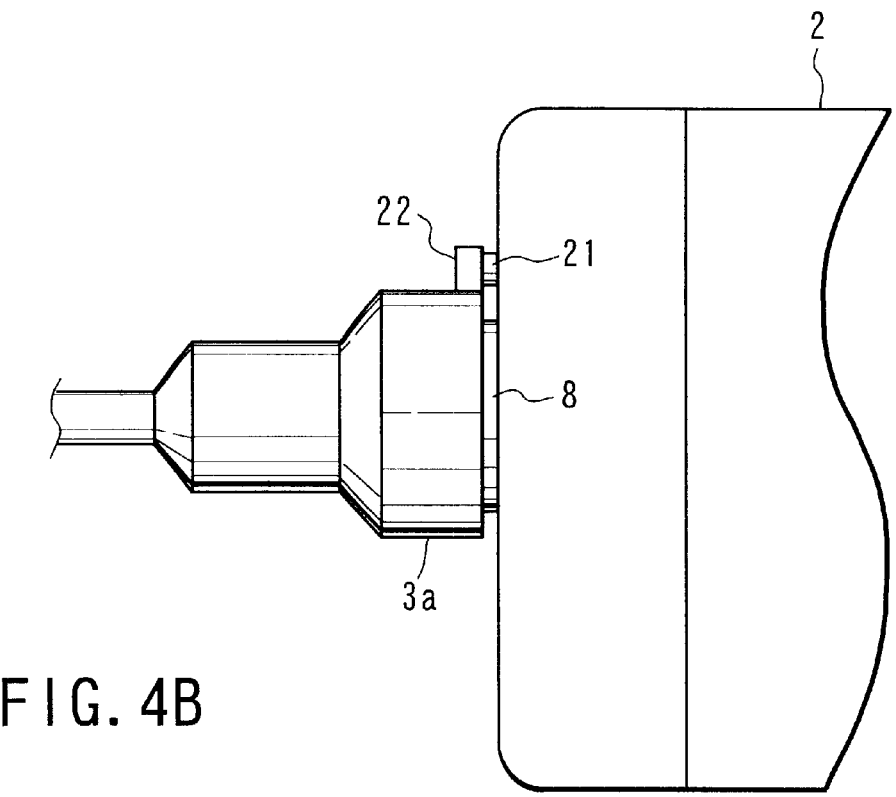

FIGS. 3, 4A and 4B relate to a second embodiment of the invention. FIG. 3 is a perspective view illustrating an external appearance of a PC base ultrasonic diagnostic apparatus according to the second embodiment. FIGS. 4A and 4B are views useful in explaining the operation of the PC base ultrasonic diagnostic apparatus of FIG. 3.

The second embodiment is basically similar to the first embodiment, and hence only different points will be described. In the first and second embodiments, like reference numerals denote like elements.

As is shown in FIG. 3, a scope attachment/detachment switch 21 is provided near a scope-side connector 3a. The scope-side connector 3a has a flange 22 for receiving the scope attachment/detachment switch 21 when the ultrasonic scope 3 is connected to the apparatus main body 2. The flange 22 has a size that enables turn-on of the scope attachment/detachment switch 21 after the ultrasonic scope 3 is electrically connected to the main body 2 (i.e. after the terminal of the connector section 8 is brought into contact with that of the scope-side connector 3a). The other structure of the second embodiment is the same as that of the first embodiment.

The operation of the second embodiment will be described. Where the scope-side connector 3a is not connected to the connector section 8, the scope attachment/detachment switch 21 is in the OFF state. After turning on the power switch 7 to excite the apparatus main body 2, and connecting the scope-side connector 3a to the connector section 8 (FIG. 4A), thereby electrically connecting the ultrasonic scope 3 to the apparatus main body 2 (bringing the terminal of the connector 3a into contact with that of the connector section 8), the flange 22 of the connector 3a turns on the scope attachment/detachment switch 21 (FIG. 4B), thereby starting the supply of power to the connector section 8.

When exchanging scopes, the scope-side connector 3a is detached from the connector section 8. At this time, at first, the pushing of the scope attachment/detachment switch 21 by the flange 22 is released to thereby turn off the switch 21 and hence stop the supply of power to the connector section 8. After that, the ultrasonic scope 3 is electrically disconnected from the apparatus main body 2 (the terminal of the connector section 8 is disconnected from that of the scope-side connector 3a). The other operation of the second embodiment is similar to that of the first embodiment.

As described above, the second embodiment has, as well as an advantage similar to that of the first embodiment, the advantage that the supply of power to the connector section 8 is controlled in synchronism with the attachment and detachment of the ultrasonic scope 3 to and from the apparatus main body 2. Therefore, the operability is further enhanced.

(Third Embodiment)

Figure 5:
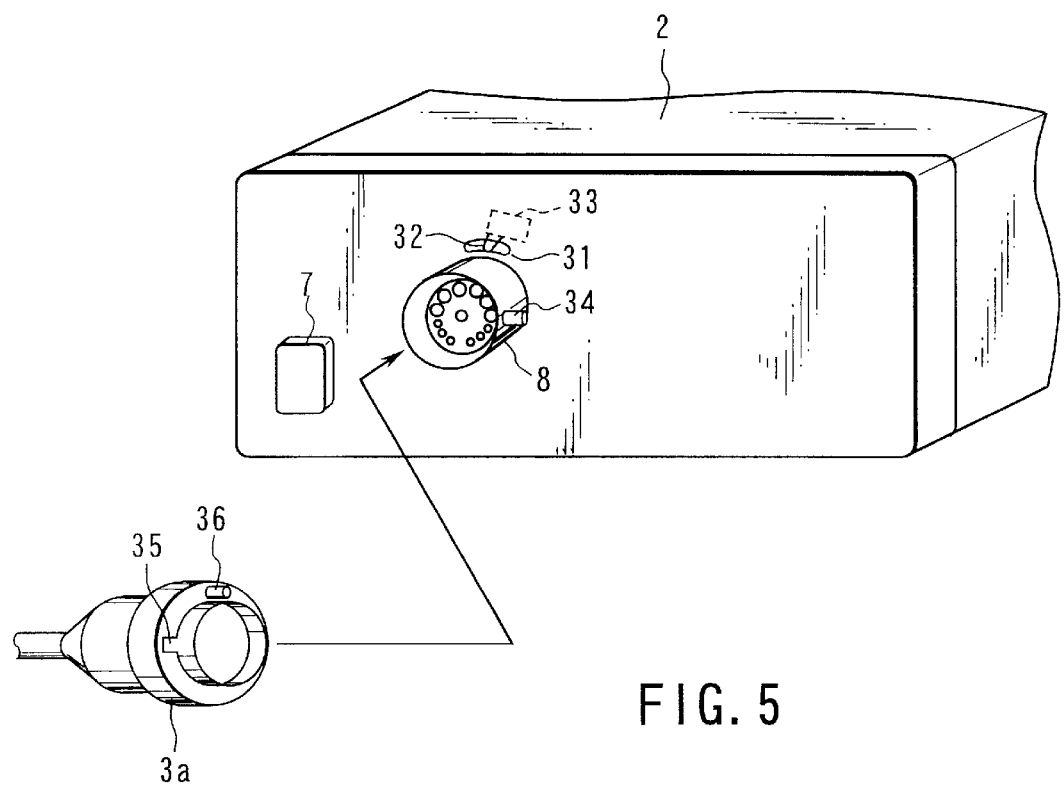
FIG. 5 is a perspective view illustrating an external appearance of a PC base ultrasonic diagnostic apparatus according to a third embodiment of the invention.

FIGS. 5, 6A, 6B, 7A, 7B, 8A and 8B relate to a third embodiment of the invention. FIG. 5 is a perspective view illustrating an external appearance of a PC base ultrasonic diagnostic apparatus according to the third embodiment. FIGS. 6A to 6C are views useful in explaining the operation of the PC base ultrasonic diagnostic apparatus of FIG. 5.

The third embodiment is basically similar to the first embodiment, and hence only different points will be described. In the first and third embodiments, like reference numerals denote like elements.

As is shown in FIG. 5, an opening 31 is formed in the apparatus main body 2 near the connector section 8, and a switch 33 is provided in the apparatus main body 2 such that a lever 32 urged in an initial position is situated in the opening 31. The connector section 8 has an engagement pin 34, while the scope-side connector 3a has an engagement groove 35 to be engaged with the engagement pin 34 when the connector 3a is connected to the connector section 8, and a pin 36 provided thereon in a position corresponding to the opening 31 and inserted in the opening 31 when the connector 3a is connected to the connector section 8. The other structure of the third embodiment is the same as that of the first embodiment.

The operation of the third embodiment will be described. The power switch 7 is turned on to excite the apparatus main body 2, and the scope-side connector 3a is connected to the connector section 8 (FIG. 6A). As a result, the ultrasonic scope 3 is electrically connected to the apparatus main body 2 (the terminal of the connector section 8 is brought into contact with that of the scope-side connector 3a), the pin 36 of the connector 3a is inserted into the opening 31, and the engagement pin 34 of the connector section 8 is engaged with the engagement groove 35 of the connector 3a (FIG. 7A).

After that, the scope-side connector 3a is rotated in a direction indicated by the arrow shown in FIG. 7A. As a result, the connector 3a is locked on the connector section 8 by the engagement pin 34, and the pin 36 moves the lever 32 urged in the initial position when the switch 33 is in the OFF state, thereby turning on the switch 33 (FIG. 8A) and starting the supply of power to the connector section 8.

When detaching the scope-side connector 3a form the connector section 8 to exchange the ultrasonic scope 3 for another, at first, the connector 3a is rotated in a direction opposite to the direction indicated by the arrow of FIG. 7A. At this time, the pin 36 moves and shifts the lever 32 to the initial position, thereby turning off the switch 33 and interrupting the supply of power to the connector section 8. On the other hand, the engagement groove 35 of the connector 3a is returned to the engagement pin 34 of the connector section 8, thereby releasing the locked state. Then, the connector 3a is detached and the ultrasonic scope 3 is electrically disconnected from the apparatus main body 2 (the terminals of the connector section 8 and the connector 3a are separated from each other). The other operation is the same as that of the first embodiment.

As described above, the third embodiment has, as well as an advantage similar to that of the first embodiment, the advantage that the supply of power to the connector section 8 is controlled in synchronism with the attachment and detachment of the ultrasonic scope 3 to and from the apparatus main body 2, thereby enhancing the operability of the apparatus, and the advantage that the lock mechanism prevents the ultrasonic scope 3 from being unintentionally detached from the apparatus main body 2 while it is used.

(Fourth Embodiment)

Figure 9:
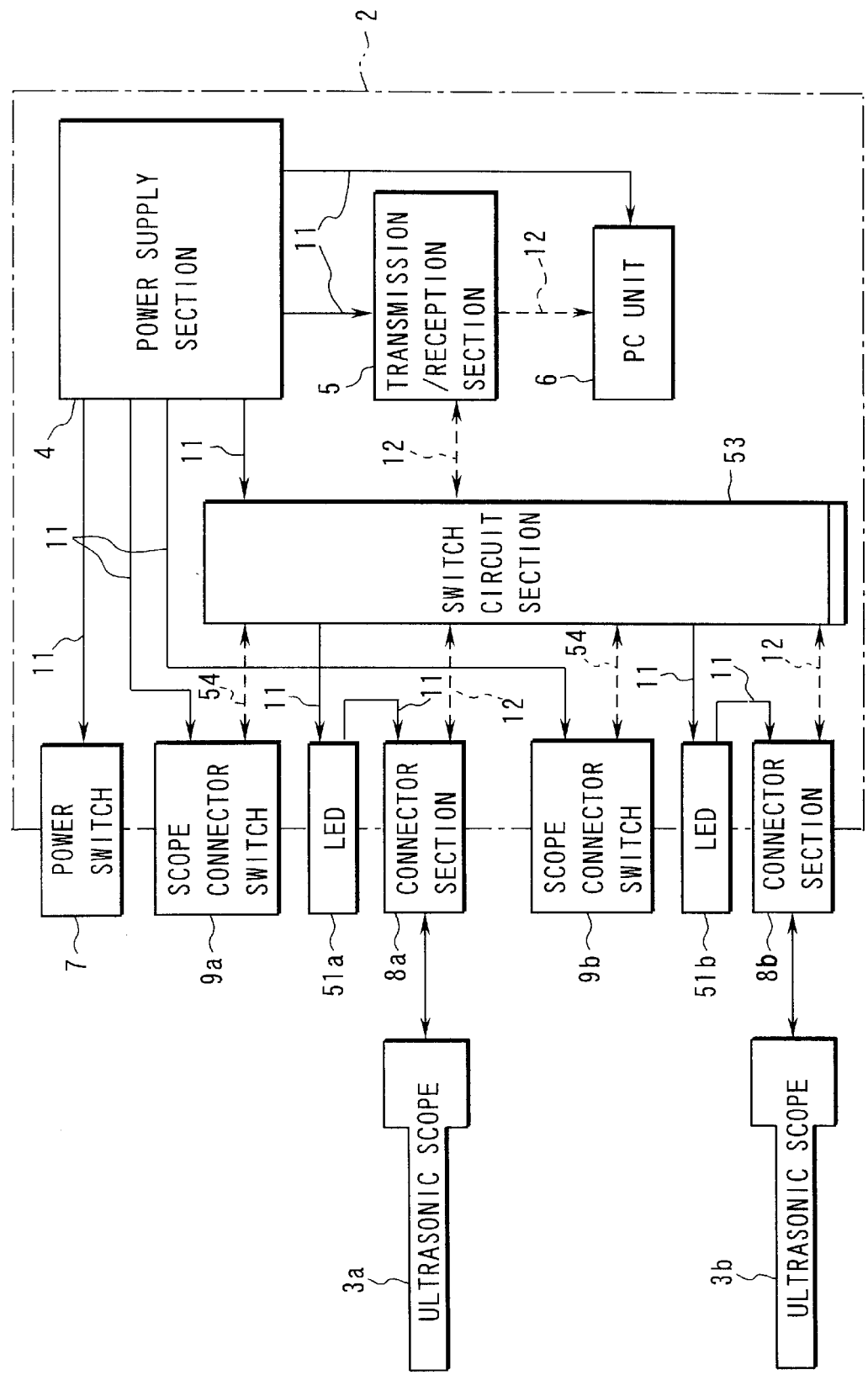
FIG. 9 is a perspective view illustrating an external appearance of the PC base ultrasonic diagnostic apparatus of FIG. 1 according to a fourth embodiment of the invention.
Figure 10:
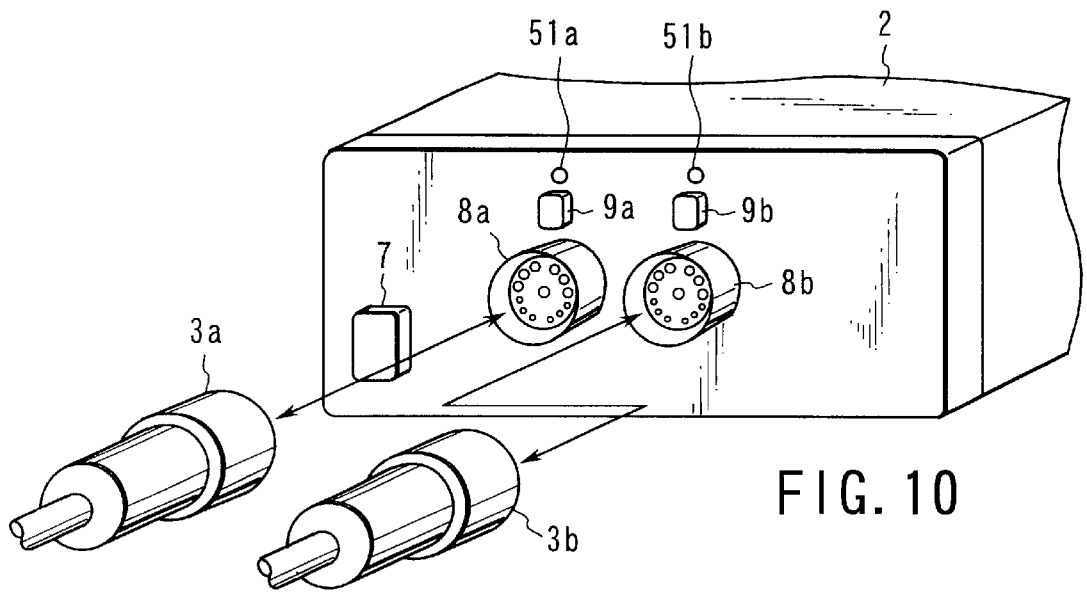
FIG. 10 is a perspective view illustrating an external appearance of the PC base ultrasonic diagnostic apparatus of FIG. 9.

FIGS. 9 and 10 relate to a fourth embodiment of the invention. FIG. 9 is a block diagram showing a PC base ultrasonic diagnostic apparatus according to the fourth embodiment, while FIG. 10 is a perspective view illustrating an external appearance of the PC base ultrasonic diagnostic apparatus of FIG. 9.

The fourth embodiment is basically similar to the first embodiment, and hence only different points will be described. In the first and fourth embodiments, like reference numerals denote like elements.

As is shown in FIG. 9, the apparatus main body 2 comprises two connector sections 8a and 8b to be connected to ultrasonic scopes 3a and 3b, respectively, and scope connector switches 9a and 9b located near the connector sections 8a and 8b, respectively. Further, LEDs 51a and 51b for indicating whether or not power is supplied to the connector sections 8a and 8b are provided on the main body 2 near the connector sections 8a and 8b, respectively.

The apparatus main body 2 contains a switch circuit section 53 for switching the supply of power to the connector sections 8a and 8b, and switching the transmission of a signal between the connector sections 8a and 8b and the transmission/reception section 5. The connector sections 8a and 8b are connected to the power supply section 4, via the switch circuit section 53 and the LEDs 51a and 51b, by means of power supply lines 11 for supplying power thereto.

The connector sections 8a and 8b are connected to the transmission/reception section 5, via the switch circuit section 53, by a signal line 12 for transmitting a transmission pulse signal to the oscillator of each ultrasonic scope 3a or 3b, and receiving a reflection signal generated from the oscillator. The scope connector switches 9a and 9b are connected to the switch circuit section 53 by respective switch signal lines 54.

FIG. 10 shows the external appearance of the main body 2 including the connector sections 8a and 8b and their peripheries. The LEDs 51a and 51b and the scope connector switches 9a and 9b are provided near the connector sections 8a and 8b, respectively. The other structure is similar to that of the first embodiment.

The operation of the fourth embodiment will be described. When using two types of ultrasonic scopes 3a and 3b as shown in FIG. 10, the connector sections 8a and 8b are connected to the ultrasonic scopes 3a and 3b, respectively. Where the ultrasonic scope 3a to be used first is connected to the connector section 8a, when the scope connector switch 9a has been pushed, a signal indicating the push of the switch 9a is transmitted to the switch circuit section 53 through one of the switch signal lines 54. The switch circuit section 53, in turn, causes power to be supplied to the connector section 8a. When the supply of power to the connector section 8 starts, the LED 51a turns on and indicates that the connector section 8a is being supplied with power. The switch circuit section 53 also switches connection to the transmission/reception section 5, thereby enabling the use of the ultrasonic scope 3a connected to the connector section 8a.

When switching the apparatus to use the ultrasonic scope 8b, the scope connector switch 9b is pushed. Then, a signal indicating the push of the switch 9b is transmitted to the switch circuit section 53 through the other switch signal line 54. The switch circuit section 53, in turn, causes power to be supplied to the connector section 8b, and interrupts the supply of power to the connector section 8a. Then, the LED 51b turns on to indicate that the connector section 8b is being supplied with power, while the LED 51a turns off to indicate that the connector section 8a is not supplied with power.

The switch circuit section 53 also switches connection to the transmission/reception section 5, thereby enabling the use of the ultrasonic scope 3b connected to the connector section 8b. It is a matter of course that, at this time, the ultrasonic scope 3a connected to the connector section 8a can be detached safely. The other operation is the same as that of the first embodiment.

As described above, the fourth embodiment has, as well as an advantage similar to that of the first embodiment, the advantage that, when using a plurality of ultrasonic scopes, the LEDs enable the operator to easily confirm which connector is being supplied with power, and hence which ultrasonic scope can be detached safely. As a result, the operability of the apparatus is enhanced.

(Fifth Embodiment)

Figure 11:
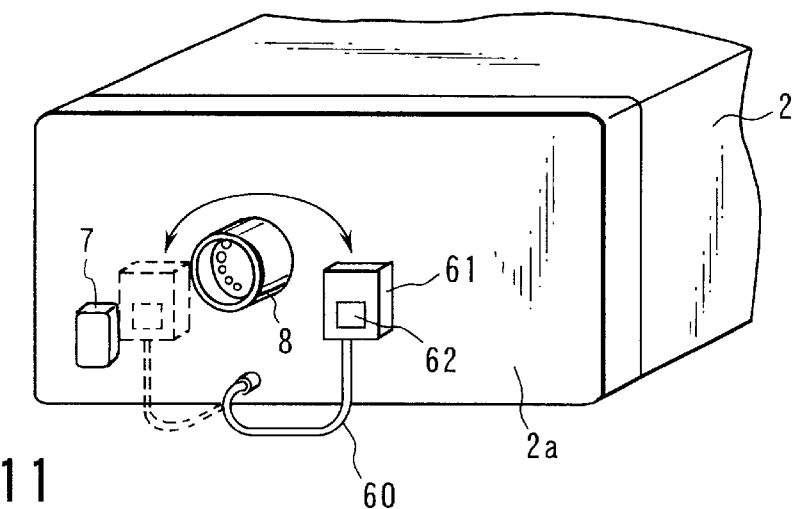
FIG. 11 is a perspective view illustrating an external appearance of a PC base ultrasonic diagnostic apparatus according to a fifth embodiment of the invention.
Figure 12A:
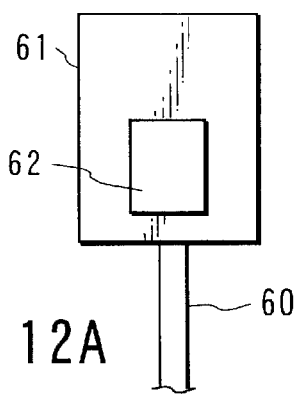
FIG. 12A is a front view of a switch box incorporated in the fifth embodiment.
Figure 12B:
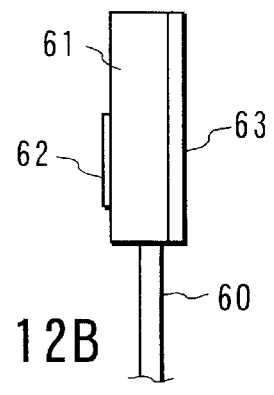
FIG. 12B is a side view of the switch box incorporated in the fifth embodiment.

FIGS. 11, 12A and 12B relate to a fifth embodiment of the invention. FIG. 11 is a perspective view illustrating an external appearance of a PC base ultrasonic diagnostic apparatus according to the fifth embodiment. FIGS. 12A and 12B are respectively front and side views of a scope connector switch incorporated in the PC base ultrasonic diagnostic apparatus of FIG. 11.

The fifth embodiment is basically similar to the first embodiment, and hence only different points will be described. In the first and fifth embodiments, like reference numerals denote like elements.

As is shown in FIG. 11, the apparatus main body 2 has a front panel 2a formed of a magnetic material such as a metal and provided with the connector section 8. A cable 60 is led from the front panel 2a and electrically connected to the power supply line 11 that is also connected to the power supply section 4 of the main body 2.

A switch box 61 is connected to at an end of the cable 60, and a scope connector switch 62 to be operated by the operator when attaching and detaching the ultrasonic scope is provided on the front surface of the switch box 61. A permanent magnet 63 is mounted on the rear surface of the switch box 61 for enabling the switch box 61 to be magnetically attached to any desired portion of the front panel 2a. The operation of the fifth embodiment is the same as that of the first embodiment, and therefore no detailed description will be given thereof.

As described above, the fifth embodiment has, as well as an advantage similar to that of the first embodiment, the advantage that the scope connector switch 62 can be detachably fixed to any desired portion of the main body, which more enhances the operability of the apparatus.

(Sixth Embodiment)

Figure 13:
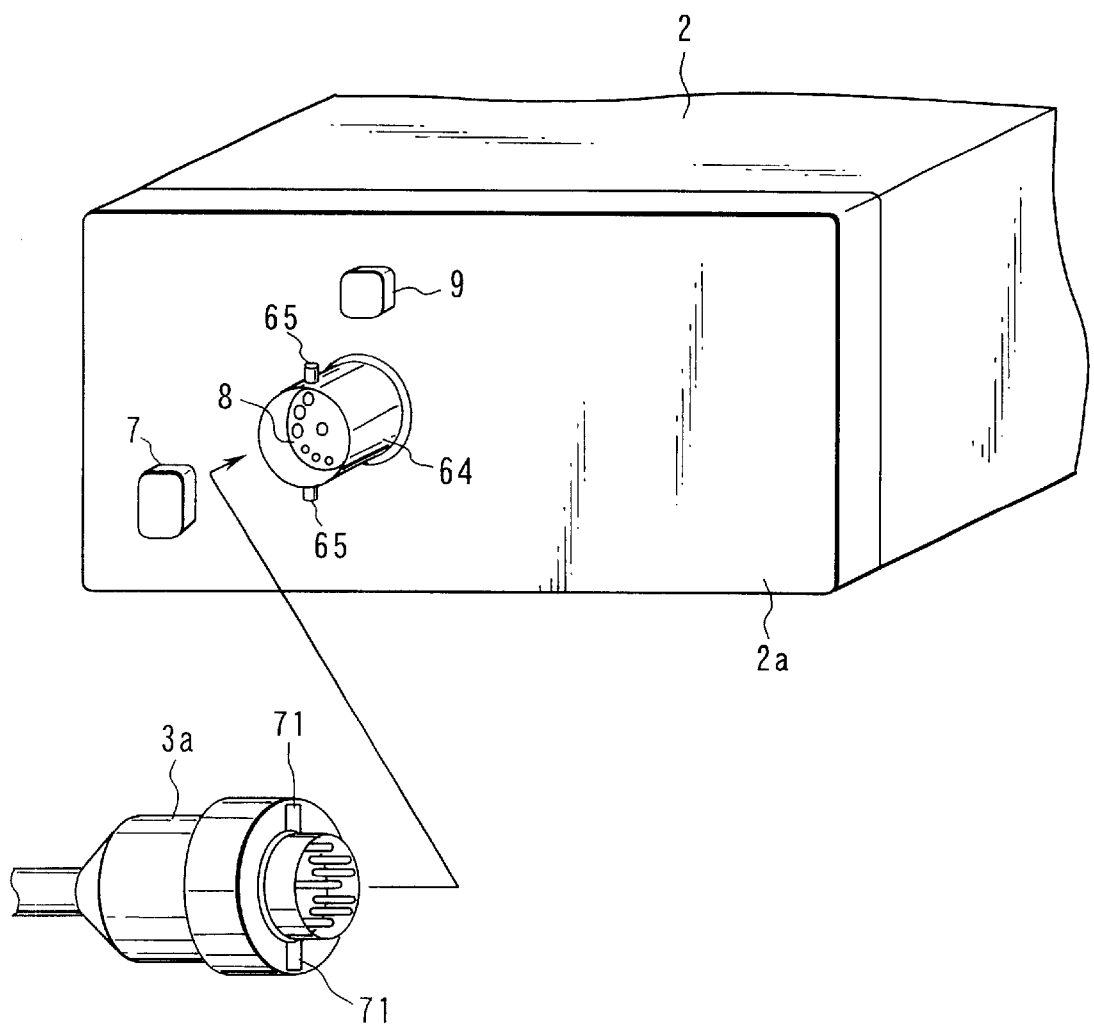
FIG. 13 is a perspective view illustrating an external appearance of a PC base ultrasonic diagnostic apparatus according to a sixth embodiment of the invention.

FIGS. 13, 14A to 14D relate to a sixth embodiment of the invention. FIG. 13 illustrates an external appearance of a PC base ultrasonic diagnostic apparatus according to the sixth embodiment and that of a scope-side connector incorporated therein. FIGS. 14A to 14D are longitudinal sectional views useful in explaining the state of connection between the scope-side connector and a connector section.

The sixth embodiment is basically similar to the first embodiment, and hence only different points will be described. In the first and sixth embodiments, like reference numerals denote like elements.

As is shown in FIGS. 13, 14A to 14D, a sleeve 64 is provided around the connector section 8 on the front panel 2a of the apparatus main body 2 such that it can move forwardly and backwardly. Engagement pins 65 projecting to the outside are provided on lower and upper portions of the distal end of the sleeve 64. The proximal end of the sleeve 64 is connected to a solenoid 66 fixed to an internal portion of the main body 2 such that the sleeve 64 is moved forwardly and backwardly by the solenoid 66.

A ring 69 is rotatably provided on the scope-side connector 3a around a terminal block 68 having a terminal 67. An annular groove 70 is formed in an inner circumferential portion of the rear end of the ring 69. Respective grooves 71, through which the engagement pins 65 can pass, are formed in those portions of a rear end wall that defines the annular groove 70, which correspond to engagement pins 65.

Figure 14A:
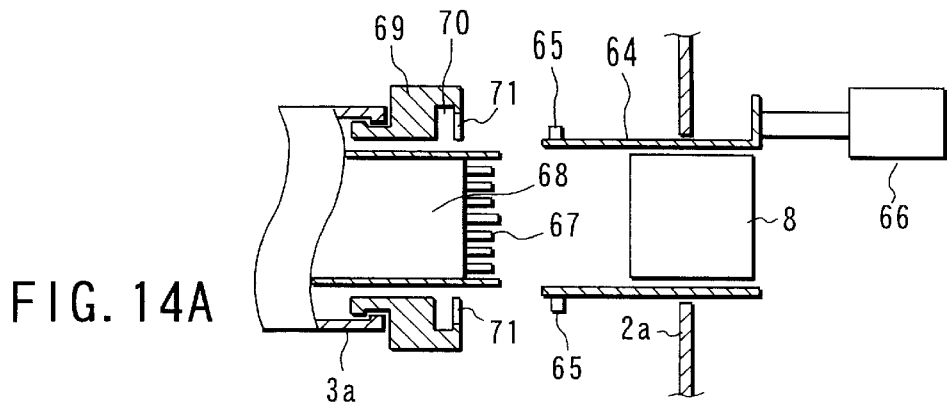
FIGS. 14A–14D are longitudinal sectional views useful in explaining the operation of the sixth embodiment.
Figure 14B:
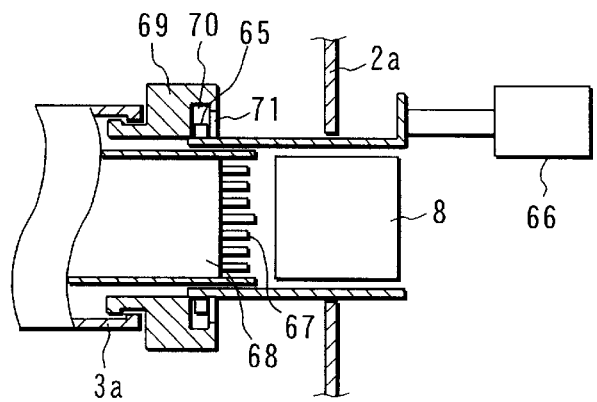

The operation of the sixth embodiment will be described. At first, the power switch 7 is turned on to excite the apparatus main body 2. Where the solenoid 66 is in the OFF state, the sleeve 64 is in its advanced position as shown in FIG. 14A. In this state, the engagement pins 65 of the sleeve 64 are aligned with the grooves 71 of the ring 69. Subsequently, as shown in FIG. 12B, the scope-side connector 3a is moved toward the connector section 8, thereby passing the engagement pins 65 through the grooves 71 and engaging them with the annular groove 70.

Figure 14C:
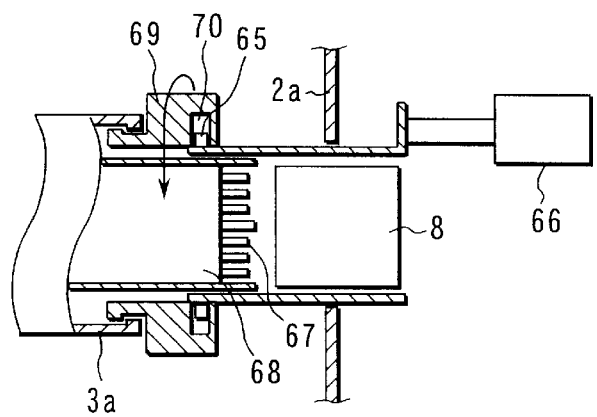
Figure 14D:
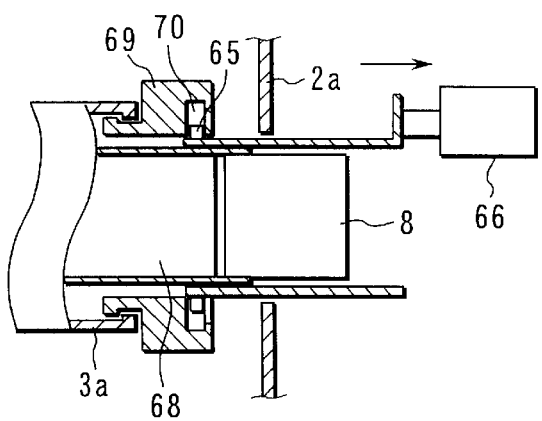

After that, the ring 69 is rotated in a direction indicated by the arrow shown in FIG. 14C, thereby locking the engagement pins 65 in the annular groove 70. If, in this state, the scope connector switch 9 is turned on, the solenoid 66 is excited to thereby pull the sleeve 64 and the ring 69 engaged with the engagement pins 65. As a result, the terminal 67 of the terminal block 68 is electrically connected to the connector section 8.

After the ultrasonic scope 3 is thus electrically connected to the apparatus main body 2 (i.e. after the terminal of the connector section 8 is brought into contact with the terminal 67 of the scope-side connector 3a), power is supplied to the connector section 8.

When the scope connector switch 9 is turned off to exchange scopes, the supply of power to the connector section 8 is interrupted, thereby demagnetizing the solenoid 66 and causing the sleeve 64 to project. Accordingly, the scope-side connector 3a is also separated from the connector section 8 by the ring 69 engaged with the engagement pins 65, and the terminal 67 of the terminal block 68 is separated from the connector section 8 and hence electrically disconnected therefrom.

In this state, the ring 69 is rotated in a direction opposite to the direction shown in FIG. 14C, to thereby align the grooves 71 of the ring 69 with the engagement pins 65. Thus, the ring 69 becomes separable from the sleeve 64. The other operation of this embodiment is the same as that of the first embodiment.

As described above, the sixth embodiment has, as well as an advantage similar to that of the first embodiment, the advantage that the ultrasonic scope 3 cannot be attached to or detached from the apparatus main body 2 while power is supplied to the connector section 8, which means that unintentional detachment of the ultrasonic scope 3 from the apparatus main body 2 can be avoided while the apparatus is used.

(Seventh Embodiment)

Figure 15A:
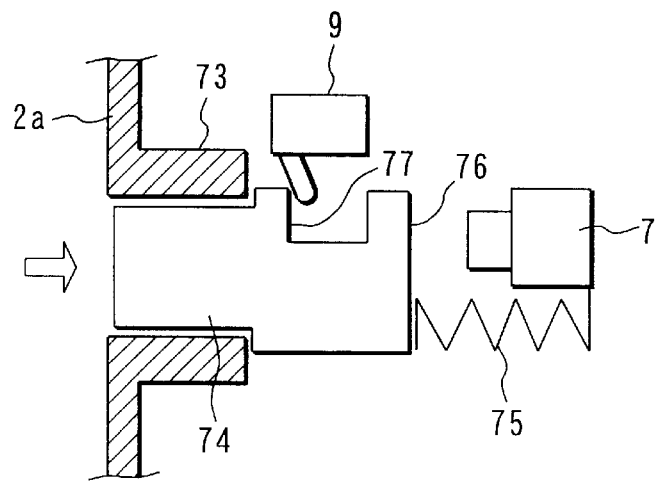
FIGS. 15A–15C are longitudinal sectional views useful in explaining the operation of a seventh embodiment.
Figure 15B:
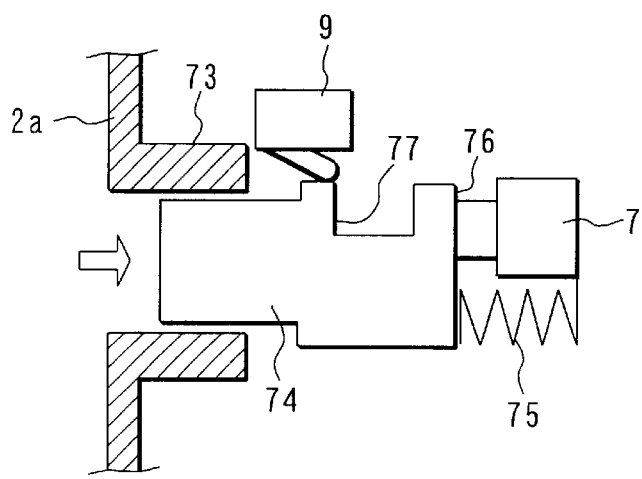
Figure 15C:
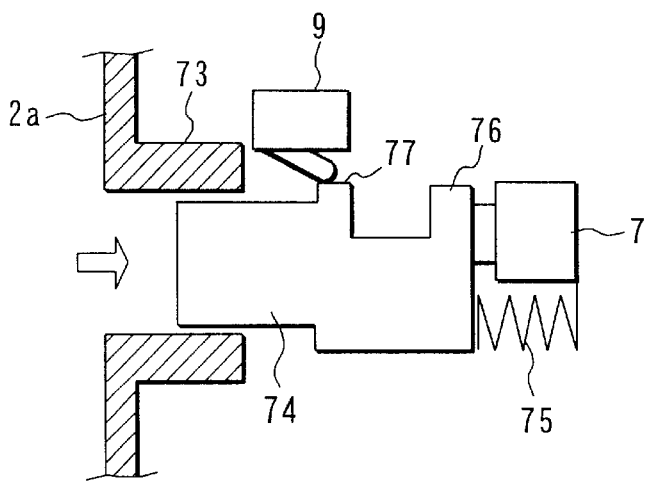

FIGS. 15A to 15C are longitudinal sectional views illustrating a PC base ultrasonic diagnostic apparatus according to a seventh embodiment of the invention, and useful in explaining the operation of a two-step push button employed in the apparatus. In the first and seventh embodiments, like reference numerals denote like elements, and no detailed description will be given of the like elements.

A switch holding cylinder 73 is provided on the front panel 2a of the apparatus main body 2. The cylinder 73 contains a two-step push button 74 to be manually pushed. The two-step push button 74 is forwardly urged by a spring 75, and has a first switch operating section 76 provided at the rear end thereof opposed to the power switch 7. The push button 74 also has a second switch operating section 77 formed of a projection and opposed to the scope connector switch 9.

The operation of the seventh embodiment will be described. In FIG. 15A, the two-step push button 74 is in its restored state caused by the urging force of the spring 75, and the power switch 7 and the scope connector switch 9 are in their OFF state. When the two-step push button 74 has been manually pushed by one step, the scope connector switch 9 is turned on by the second switch operating section 77 as shown in FIG. 15B. As a result, power is supplied to the connector section 8. In this state, however, the power switch 7 is kept OFF since the first switch operating section 76 does not push it.

When the two-step push button 74 has been manually pushed by two steps, the first switch operating section 76 pushes the power switch 7 while the second switch operating section 77 keeps the scope connector switch 9 in the ON state. As a result, the power switch is turned on. Thereafter, the two-step push button 74 returns to its restored state as shown in FIG. 15A caused by the urging force of the spring 75.

When exchanging scopes, the two-step push button 74 has been manually pushed by one step. As a result, the scope connector switch 9 is turned off by the second switch operating section 77 as shown in FIG. 15B. At this time, the power switch 7 is kept ON since the first switch operation section 76 does not push it. Thereafter, the two-step push button 74 returns to its restored state as shown in FIG. 15A caused by the urging force of the spring 75.

After exchanging scopes, the two-step push button 74 has been manually pushed by one step. As a result, the scope connector switch 9 is turned on by the second switch operation section 77 as shown in FIG. 15B. At this time, the power switch 7 is kept ON since the first switch operation section 76 does not push it. Thereafter, the two-step push button 74 returns to its restored state as shown in FIG. 15A caused by the urging force of the spring 75.

When turning off the power switch 7, the two-step push button 74 has been manually pushed by two step, the scope connector switch 9 is firstly turned off by the second switch operating section 77 as shown in FIG. 15B. And then the first switch operating section 76 pushes the power switch 7, therefore the power switch turned off as shown in FIG. 15C.

The seventh embodiment has, as well as an advantage similar to that of the first embodiment, the advantage that the switch operation is simple and hence the apparatus has a high operability.

(Eighth Embodiment)

Figure 16:
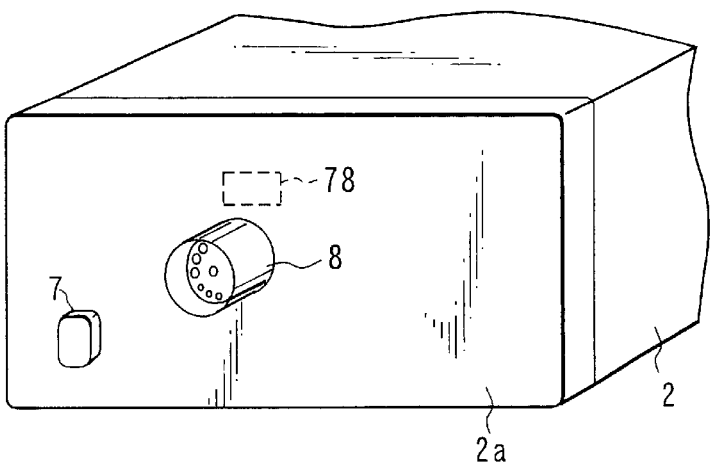
FIG. 16 is a perspective view illustrating an external appearance of a PC base ultrasonic diagnostic apparatus according to an eighth embodiment of the invention.
Figure 17:
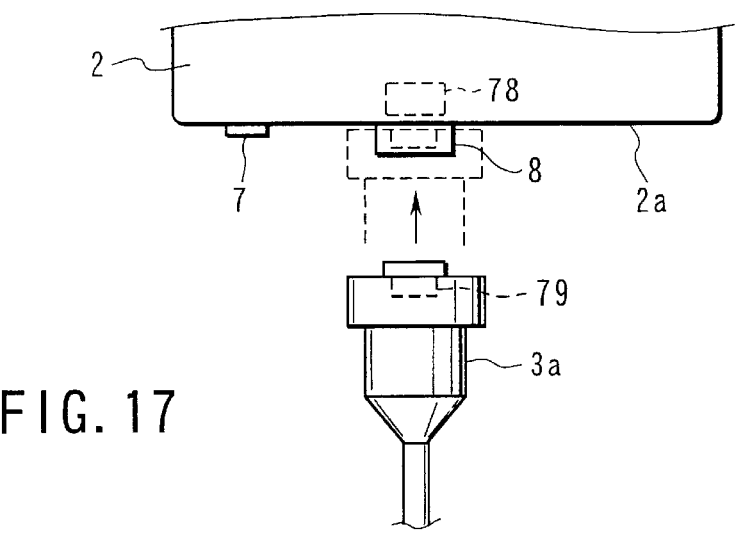
FIG. 17 is a plan view of the PC base ultrasonic diagnostic apparatus according to the eighth embodiment.

FIGS. 14 and 15 relate to a PC base ultrasonic diagnostic apparatus according to an eighth embodiment of the invention. FIG. 16 is a perspective view of the apparatus, while FIG. 17 is a plan view of the same. In the first and eighth embodiments, like reference numerals denote like elements, and no detailed description will be given of the like elements.

A magnet switch 78 is provided on the inner surface of the front panel 2a of the apparatus main body 2 near the connector section 8. On the other hand, a permanent magnet 79 is provided on the front surface of the scope-side connector 3a to be attached to and detached from the connector section 8.

The operation of the eighth embodiment will be described. At first, the power switch 7 is turned on to excite the apparatus main body 2. After that, the scope-side connector 3a is connected to the connector section 8. At this time, the permanent magnet 79 provided on the connector 3a is situated close to the magnet switch 78, and therefore the switch 78 is turned on by the magnetism of the permanent magnet 79, thereby starting the supply of power to the connector section 8.

The eighth embodiment has, as well as an advantage similar to that of the first embodiment, the advantage that the switch operation is simple and hence the apparatus has a high operability.

(Ninth Embodiment)

Figure 18:
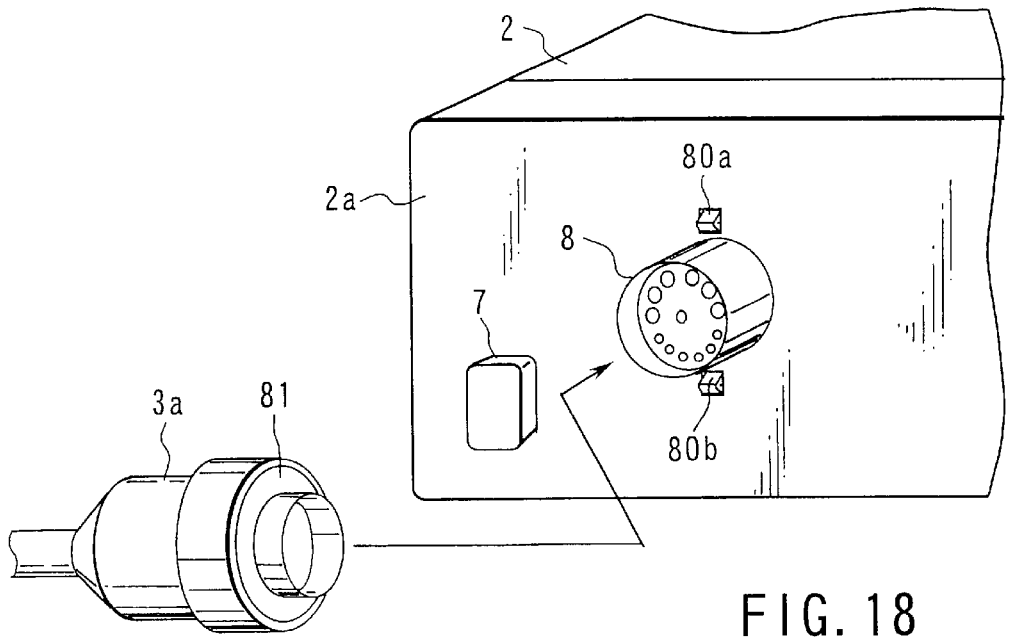
FIG. 18 is a perspective view illustrating an external appearance of a PC base ultrasonic diagnostic apparatus according to a ninth embodiment of the invention.
Figure 19:
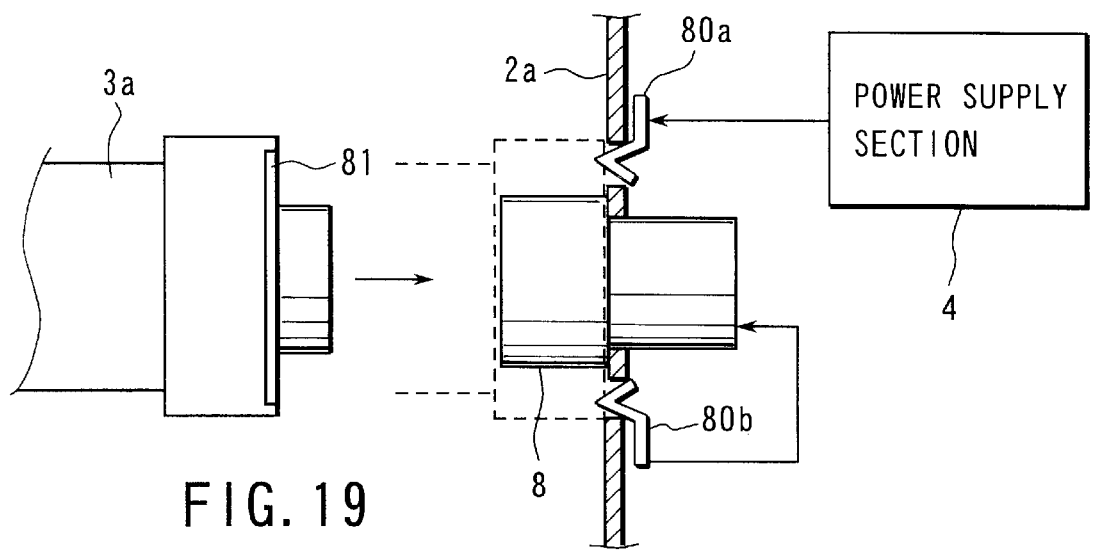
FIG. 19 is a longitudinal sectional view showing the PC base ultrasonic diagnostic apparatus of the a ninth embodiment.

FIGS. 18 and 19 relate to a PC base ultrasonic diagnostic apparatus according to a ninth embodiment of the invention. FIG. 18 is a perspective view showing an apparatus main body 2 and a scope-side connector 3a incorporated in the apparatus. FIG. 19 is a longitudinal sectional view showing the apparatus main body 2 and the scope-side connector 3a. In the first and ninth embodiments, like reference numerals denote like elements, and no detailed description will be given of the like elements.

A pair of contacts 80a and 80b formed of respective plate springs are provided on the outer surface of the front panel 2a of the apparatus main body 2 near the connector section 8. One of the contacts 80a and 80b is electrically connected to the power supply section 4, while the other contact is electrically connected to the connector section 8.

A ring-shaped conductive section 81 is provided on the front surface of the scope-side connector 3a to be attached to and detached from the connector section 8.

The operation of the ninth embodiment will be described. At first, the power switch 7 is turned on to excite the apparatus main body 2. After that, the scope-side connector 3a is connected to the connector section 8. At this time, the conductive section 81 on the scope-side connector 3a is brought into contact with the contacts 80a and 80b on the front panel 2a and hence electrically connected thereto. As a result, power is supplied to the connector section 8.

The ninth embodiment has, as well as an advantage similar to that of the first embodiment, the advantage that the switch operation is simple and hence the apparatus has a high operability.

(Tenth Embodiment)

Figure 20:
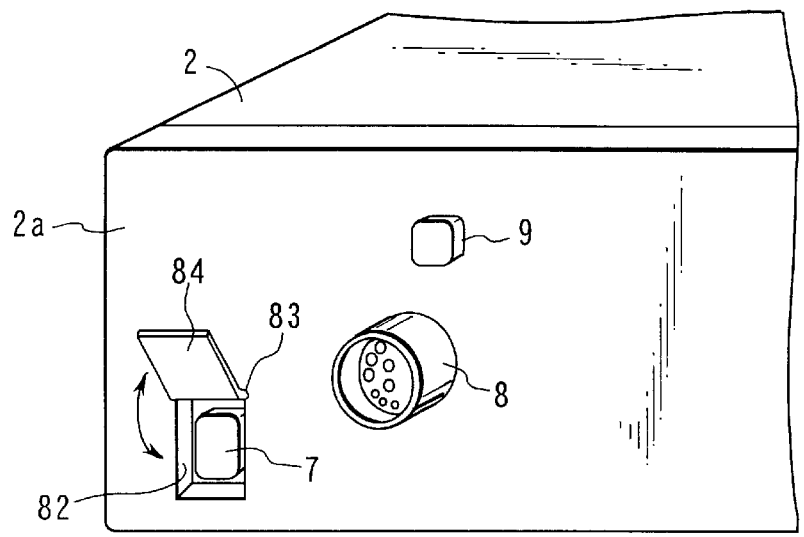
FIG. 20 is a perspective view illustrating an external appearance of a PC base ultrasonic diagnostic apparatus according to a tenth embodiment of the invention.
Figure 21:
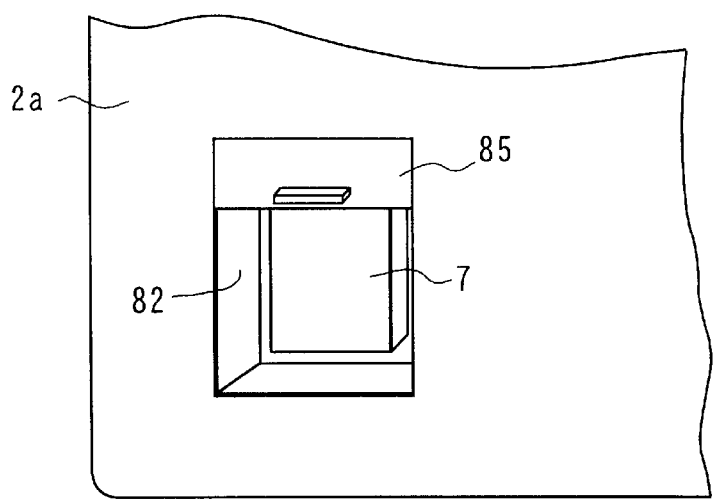
FIG. 21 is a view showing a modification of PC base ultrasonic diagnostic apparatus according to the tenth embodiment of the invention.

FIGS. 20 and 21 are perspective views illustrating a PC base ultrasonic diagnostic apparatus according to a tenth embodiment of the invention. In the first and tenth embodiments, like reference numerals denote like elements, and no detailed description will be given of the like elements.

AS shown in FIG. 20, a recession 82 is formed in the front panel 2a of the apparatus main body 2, and contains a power switch 7. A cover 84 that can swing about a hinge 83 is provided to open and close the recess 82. Further, a shutter type cover 85 as shown in FIG. 21, which can slide vertically, may be used instead of the cover 84 to open and close the recess 82.

The operation of the ninth embodiment will be described. When turning on the apparatus main body 2, at first, the cover 84 or 85 is opened to turn on the power switch 7.

Similarly, when turning off the main body 2, the cover 84 or 85 is opened to turn off the power switch 7.

The tenth embodiment is free from an erroneous operation such as unintentional turning off of the power switch 7.

(Eleventh Embodiment)

Figure 22:
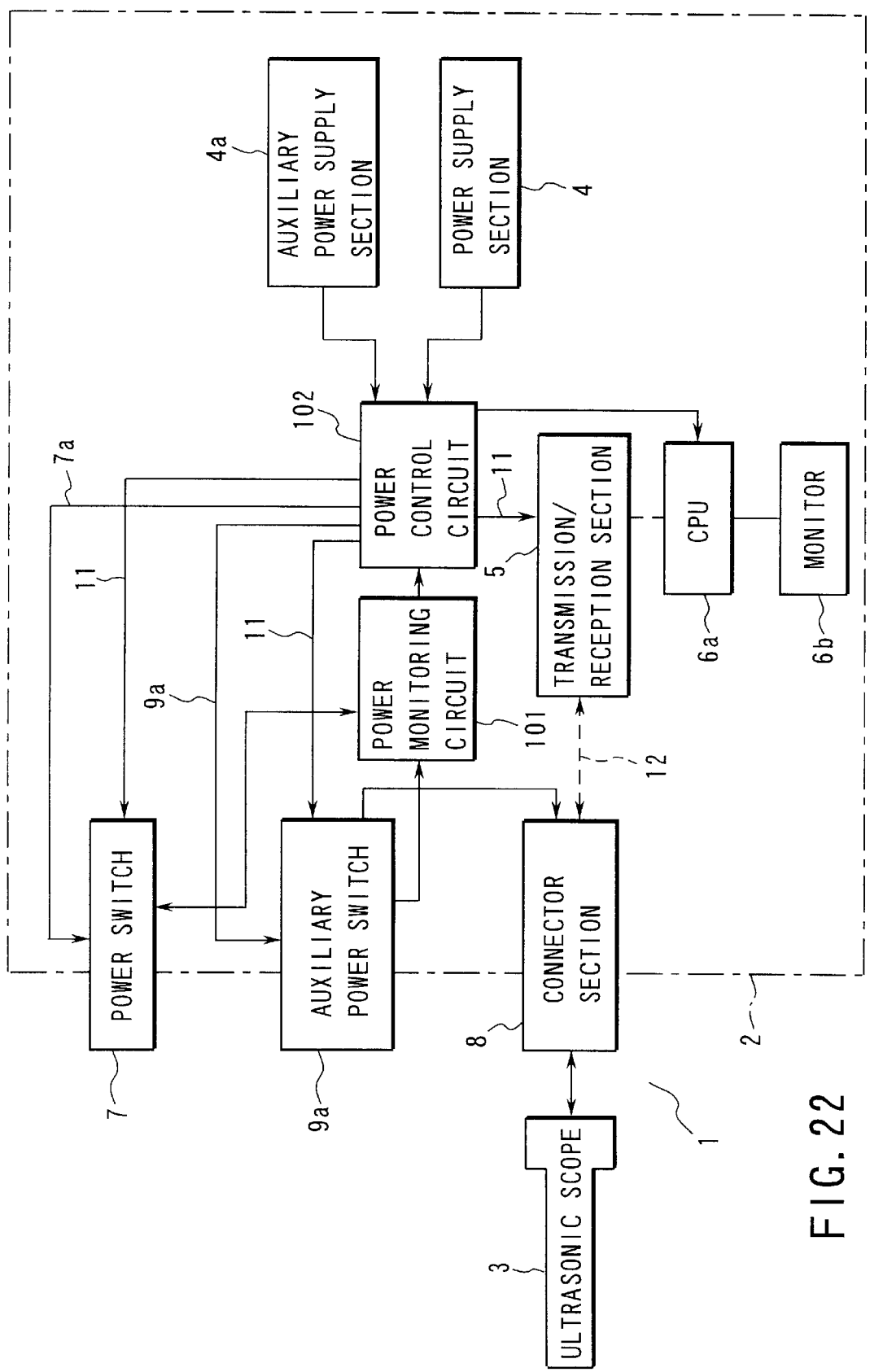
FIG. 22 is a block diagram illustrating an eleventh embodiment of the invention.
Figure 23:
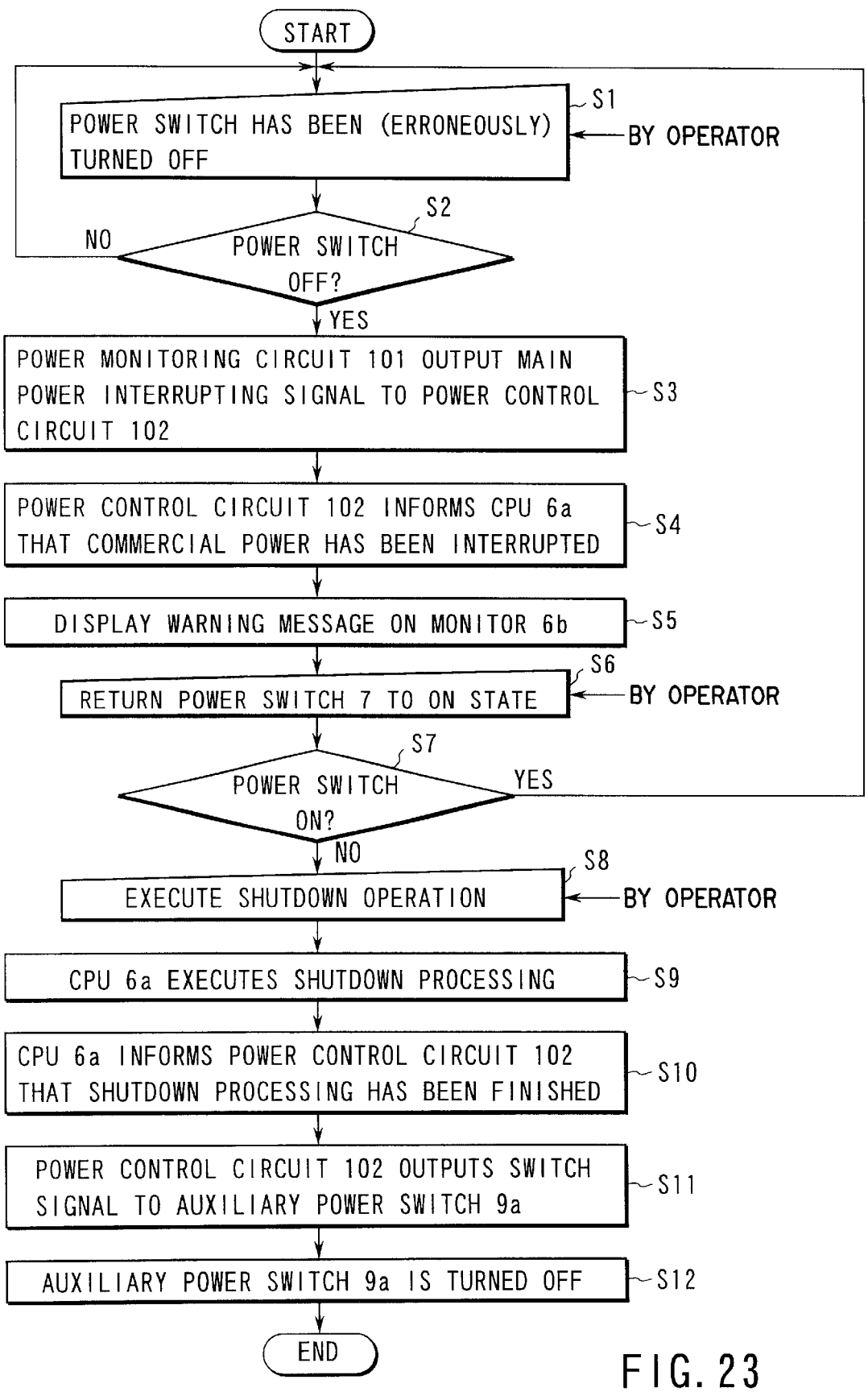
FIG. 23 is a flowchart useful in explaining termination processing executed when a power switch incorporated in the eleventh embodiment is turned off.

FIG. 22 is a block diagram illustrating a PC base ultrasonic diagnostic apparatus according to an eleventh embodiment of the invention. In the first and eleventh embodiments, like reference numerals denote like elements, and no detailed description will be given of the like elements. FIG. 23 is a flowchart useful in explaining termination processing executed when a power switch incorporated in the eleventh embodiment is turned off.

This embodiment employs a power switch 7 and an auxiliary power switch 9*a* corresponding to the scope connector switch 9 shown in FIG. 1. A power monitoring circuit 101 monitors the ON/Off states of the power switch 7 and the auxiliary power switch 9*a*. A power control circuit 102 supplies the power switch 7 or the auxiliary power switch 9*a* with main power from the power supply section 4 or auxiliary power from an auxiliary power supply section 4*a* in accordance with the ON/Off state of each of the power switch 7 and the auxiliary power switch 9*a* detected by the power monitoring circuit 101.

The power control circuit 101 executes control so that the power switch 7 turns on at the start of operation, and the auxiliary power switch 9*a* turns on when the power switch 7 is in the ON state.

Step S1 indicates a case where the operator erroneously has turned off the power switch 7. It is determined at a step S2 whether or not the power switch 7 has been turned off. If the answer is No, the program returns to the step S1, whereas if the answer is Yes, the power monitoring circuit 101 supplies, at a step S3, the power control circuit 102 with a signal indicating that the main power has been interrupted.

As a result, auxiliary power is supplied from the auxiliary power supply 4*a* to the power switch 7 under the control of the power control circuit 102.

After that, the program proceeds to a step S4, where the power control circuit 102 informs a CPU 6*a* that the commercial power has been interrupted. Then, the program proceeds to a step S5, where the CPU 6*a* causes a monitor 6*b* to display the following warning messages:

"When finishing the operation, please execute shutdown processing."

"When continuing the operation, please return the power switch 7 to the ON state."

"When exchanging probes, it is not necessary to turn off the power switch 7."

At a step S6, the operator manually returns the power switch 7 to the ON state. At a step S7, it is determined whether or not the power switch 7 has been turned on. If the answer is Yes, the program returns to the step S1, whereas if the answer is No, the program proceeds to a step S8, where the operator manually executes the shutdown operation.

After the shutdown operation has been executed at the step S8, the CPU 6*a* executes shutdown processing at a step S9. At a step S10, the CPU 6*a* informs the power control circuit 102 that the shutdown processing has been finished. At a step S11, the power control circuit 102 outputs a switchover signal to the auxiliary power switch 9*a*. If the power switch is turned on and power is supplied in the next occasion, the auxiliary power switch 9*a* is again turned on under the control of the power control circuit 102.

As described above, the eleventh embodiment is advantageous in that when the main power switch 7 has been erroneously turned off, the operator receives a warning message that when exchanging probes, it is sufficient if the auxiliary power switch 9*a* is turned off.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:

a casing;

a power supply section;

an ultrasonic scope having a connector at an end thereof and adapted to transmit and receive an ultrasonic wave;

a connector section provided at the casing to which the connector of the ultrasonic scope is detachably attached;

an auxiliary switch for allowing and interrupting supply of power from the power supply section to the connector section; and ultrasonic signal processing means for supplying the ultrasonic scope with an ultrasonic wave and processing an echo signal of the ultrasonic wave when power is supplied to the connector section.

2. The ultrasonic diagnostic apparatus according to claim 1, wherein the auxiliary switch is provided near the connector section.

3. The ultrasonic diagnostic apparatus according to claim 1, further comprising informing means for indicating whether or not power is supplied to the connector section is provided on the casing near the connector section.

4. The ultrasonic diagnostic apparatus according to claim 1, wherein the auxiliary switch turns on when the connector of the ultrasonic scope is attached to the connector section, and turns off when the connector of the ultrasonic scope is detached from the connector section.

5. The ultrasonic diagnostic apparatus according to claim 1, wherein the auxiliary switch turns on when the connector of the ultrasonic scope has been attached to the connector section and rotated in a first direction, and turns off when the connector of the ultrasonic scope has been attached to the connector section and rotated in a second direction opposite to the first direction, and further comprising a lock mechanism for preventing the connector from being disconnected from the connector section when the auxiliary switch is in an ON state.

6. The ultrasonic diagnostic apparatus according to claim 1, wherein the auxiliary switch includes a cable extending from the casing, and a switch box connected to the cable, the switch box having a permanent magnet attached to a reverse surface thereof.

7. The ultrasonic diagnostic apparatus according to claim 1, further comprising:

a solenoid having its electric conduction controlled by turn-on and -off of the auxiliary switch;

a sleeve provided on the casing around the connector section, disposed to move forward and backward in accordance with a conduction state of the solenoid, and having an engagement pin provided on an outer surface thereof; and a ring rotatably provided on the ultrasonic scope around the connector and having an annular groove and a groove formed therein, the engagement pin being able to pass through the groove.

8. The ultrasonic diagnostic apparatus according to claim 1, further comprising a power switch, the power switch and the auxiliary being operated by a two-step button.

9. The ultrasonic diagnostic apparatus according to claim 1, wherein the auxiliary switch is a magnetic switch and is turned on when the connector of the ultrasonic scope has been mounted on the connector section.

10. The ultrasonic diagnostic apparatus according to claim 1, wherein the auxiliary switch comprises:

a pair of contacts provided on the casing around the connector section, one of the contacts being connected to a main power supply, and the other of the contacts being connected to the connector section; and a conductive member provided on a front surface of the connector of the ultrasonic scope.

11. The ultrasonic diagnostic apparatus according to claim 1, further comprising a power switch provided in a recess that is defined in the casing, and an openable/closable cover or a shutter type cover for opening and closing the recess.

12. An ultrasonic diagnostic apparatus comprising:

a power supply section;

at least two connector sections, to each of which a connector of an ultrasonic scope is detachably attached;

auxiliary switches each provided for a corresponding one of the at least two connector sections for allowing and interrupting supply of power from the power supply section to the corresponding one of the connector sections; and ultrasonic signal processing means for supplying the ultrasonic scope with an ultrasonic wave and processing an echo signal of the ultrasonic wave when power is supplied to any one of the connector sections.

13. An ultrasonic diagnostic apparatus comprising:

display means;

a main power supply section;

a power switch for controlling supply of power from the main power supply section;

an auxiliary power supply section;

an ultrasonic scope having a connector at an end thereof and adapted to transmit and receive an ultrasonic wave;

a connector section to which the connector of the ultrasonic scope is detachably attached;

ultrasonic signal processing means for supplying the ultrasonic scope with an ultrasonic wave and processing an echo signal of the ultrasonic wave when power is supplied to the connector section;

an auxiliary switch for allowing and interrupting supply of power from the main power supply section to the connector section;

a power monitoring section for monitoring an ON/OFF state of each of the power switch and the auxiliary switch;

a power control section for controlling the ON/OFF state of each of the power switch and the auxiliary switch; and control means for supplying the auxiliary power to the auxiliary switch, then displaying a warning message on the display means, and returning the power switch to an ON state, when the power monitoring section has detected an OFF state of the power switch.

14. The ultrasonic diagnostic apparatus according to claim 13, wherein the warning message includes a message "it is not necessary to turn off the power switch, when exchanging probes".

* * * * *